US 9,562,851 B2

(12) United States Patent
Oberti et al.

(10) Patent No.: US 9,562,851 B2
(45) Date of Patent: Feb. 7, 2017

(54) ONBOARD DEVICE AND METHOD FOR ANALYZING FLUID IN A HEAT ENGINE

(71) Applicant: SP3H, Aix-en-Provence (FR)

(72) Inventors: Sylvain Oberti, Marseilles (FR); Johan Fournel, Robion (FR)

(73) Assignee: SP3H, Aix-en-Provence (FR)

( * ) Notice: Subject to any disclaimer, the term of this patent is extended or adjusted under 35 U.S.C. 154(b) by 0 days.

(21) Appl. No.: 14/648,874

(22) PCT Filed: Dec. 4, 2013

(86) PCT No.: PCT/FR2013/052941
§ 371 (c)(1),
(2) Date: Jun. 1, 2015

(87) PCT Pub. No.: WO2014/087103
PCT Pub. Date: Jun. 12, 2014

(65) Prior Publication Data
US 2015/0300951 A1    Oct. 22, 2015

(30) Foreign Application Priority Data

Dec. 7, 2012   (FR) .................................... 12 61757
Dec. 7, 2012   (FR) .................................... 12 61758

(51) Int. Cl.
*G01N 21/3577*    (2014.01)
*G01N 21/3504*    (2014.01)
(Continued)

(52) U.S. Cl.
CPC ........ *G01N 21/3577* (2013.01); *G01N 21/274* (2013.01); *G01N 21/3504* (2013.01);
(Continued)

(58) Field of Classification Search
CPC ........................ G01N 1/3577; G01N 1/35772
See application file for complete search history.

(56) References Cited

U.S. PATENT DOCUMENTS 6,356,774 B1 *   3/2002  Bernstein ........... A61B 5/14552
                                                         600/322
2002/0179815 A1  12/2002 Forke
(Continued)

FOREIGN PATENT DOCUMENTS

FR    2 940 447 A1    6/2010
WO    2008/129453 A1  10/2008
WO    2010/053617 A2  5/2010

OTHER PUBLICATIONS

Mar. 3, 2014 International Search Report issued in Application No. PCT/FR2013/052941.

*Primary Examiner* — Tarifur Chowdhury
*Assistant Examiner* — Omar Nixon
(74) *Attorney, Agent, or Firm* — Oliff PLC

(57) ABSTRACT

The present invention relates to a method for controlling a spectrometer for analyzing a product, the spectrometer including a light source including several light-emitting diodes having respective emission spectra covering in combination an analysis wavelength band, the method including steps of: supplying at least one of the light-emitting diodes with a supply current to switch it on, measuring a light intensity emitted by the light source by measuring a current at a terminal of at least another of the light-emitting diodes maintained off, determining, according to each light intensity measurement, a setpoint value of the supply current of each diode that is on, and regulating the supply current of each diode that is on so that it corresponds to the setpoint value.

34 Claims, 4 Drawing Sheets

Figure 1:
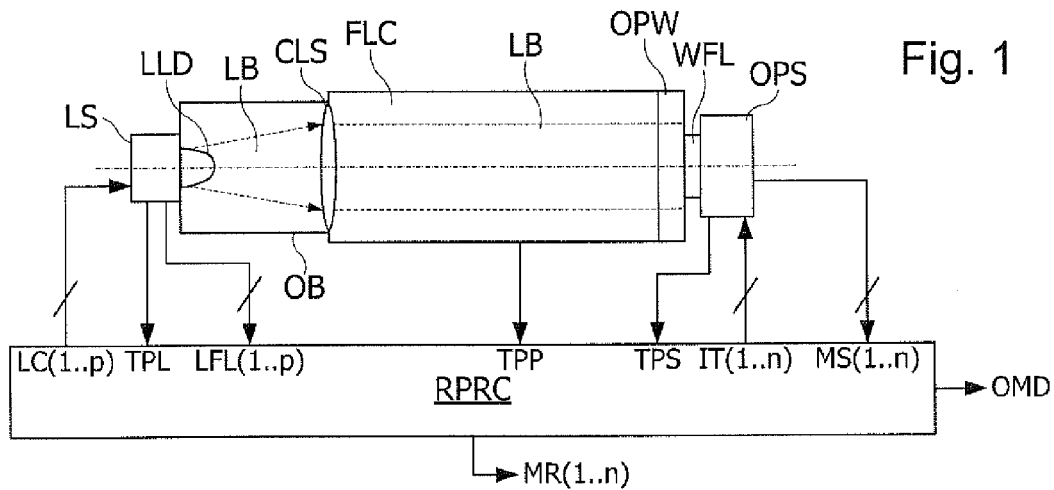

(51) Int. Cl.
*G01N 21/27* (2006.01)
*G01N 21/31* (2006.01)

(52) U.S. Cl.
CPC ............... *G01N 2021/3181* (2013.01); *G01N 2201/062* (2013.01); *G01N 2201/0624* (2013.01); *G01N 2201/121* (2013.01); *G01N 2201/124* (2013.01); *G01N 2201/127* (2013.01); *G01N 2201/1211* (2013.01); *G01N 2201/1242* (2013.01); *G01N 2201/1247* (2013.01); *G01N 2201/12723* (2013.01)

(56) References Cited

U.S. PATENT DOCUMENTS

| | | | |
|---|---|---|---|
| 2005/0083687 A1* | 4/2005 | Brass ................ | G01N 21/31 362/231 |
| 2006/0072319 A1 | 4/2006 | Dziekan et al. | |
| 2006/0121602 A1* | 6/2006 | Hoshizaki ............ | G01N 21/645 435/288.7 |
| 2008/0131836 A1* | 6/2008 | Rueggeberg ......... | A61C 13/082 433/29 |
| 2010/0305499 A1* | 12/2010 | Matsiev ................ | A61B 5/145 604/67 |
| 2011/0313635 A1* | 12/2011 | Blanc .................. | F02D 41/1451 701/102 |
| 2012/0287431 A1* | 11/2012 | Matsiev ................ | G01N 21/31 356/306 |

* cited by examiner

ONBOARD DEVICE AND METHOD FOR ANALYZING FLUID IN A HEAT ENGINE

The present invention relates to the analysis of fluids by spectrometry. The present invention applies in particular but not exclusively to analyzing fluids in a heat engine, and in particular to analyzing the hydrocarbons used as fuel in such an engine. This analysis concerns ail heat engines, whether used in land, sea or air transports, military engines or stationary engines.

The tightening of environmental standards requires the different manufacturers or users of heat engines to search for fuel consumption gains and reductions in polluting engine emissions. However, certain features of fuel, such as its composition, prove to have a direct influence on the performance and the proper operation of heat engines. It further transpires that some of these features are particularly variable as regards hydrocarbon-based fuels, in particular depending on the origin of the fuel. Indeed, it is estimated that some features such as the composition of hydrocarbon-based fuels can vary by 15 to 40% or more. However, knowing these features enables certain engine settings to be determined so as to reduce the consumption and the polluting emissions of the engine. Moreover, qualitative knowledge of fuel can also enable pollution or anomalies of the fuel to be identified, thus preventing damage to the engine or the vehicle in general.

It is thus desirable to analyze the features such as the composition of the fuel supplying a heat engine, and to take the results obtained into account to adjust the engine operating parameters. For that purpose, near-infrared spectrometry (from 700 to 2,500 nm) is suited to the analysis of hydrocarbons or hydrocarbon mixes.

A sensor based on the spectrometry principle, in particular near-infrared spectrometry, generally comprises a spectrometer and a data processing calculator enabling the raw output signals (raw spectrum) of the spectrometer to be transformed into qualitative information on the product to be measured. The spectrometer comprises a light source which covers at least one wavelength band in which the analysis must be performed, a measurement cell in which the light produced by the light source and the product to be analyzed interact, and a sensor that supplies a spectrum of the light at output of the measurement cell. The spectrometer can measure the spectrum of the product to be analyzed by the transmission, reflection or absorption of a beam of light emitted by the light source. A spectrometer is mainly characterized by its spectrum analysis range (width and position of the spectrum generated), its fineness of analysis or the number of measurement points constituting the spectrum generated, and its accuracy of measurement.

Therefore, present-day spectrometers, generally designed for laboratories or complex and expensive industrial applications, are not really suited to the environment of a heat engine, and in particular that of a motor vehicle, where they can undergo intense vibrations and extreme temperatures. In addition to their high complexity, high cost, relatively significant size and need for maintenance, these devices require numerous optical components imposing strict alignment, handling and storage requirements.

It is thus desirable to produce a spectrometer that is compatible with mass production, at a cost suited to that of automotive components, and which is adapted to the automotive environment. For this purpose, the use of one or more light-emitting diodes (LED) as light source appears to be particularly adapted.

However, it emerges that the measured spectrum, which is characteristic of the quality and/or of the composition of the product to be analyzed, is affected by external factors, such as the temperature, and by the features of the spectrum of the light beam interacting with the product to be analyzed. Now, LED diodes age, so their emission spectrum varies over time as explained in the article of the LED Journal "LED lighting Life Prediction" by Jianzhong Jiao, Ph.D., Director of Regulations & Emerging Technologies, Osram Opto Semiconductors, Inc., October 2009. In addition, it is well-known and proven that near-infrared spectrometry is generally sensitive to temperature (as explained for example in the publication "On-line monitoring of batch cooling crystallization of organic compounds using ATR-FTIR spectroscopy coupled with an advanced calibration method"—Chemometrics and intelligent Laboratory Systems 96 (2009) 49-58, Zeng-Ping Chen, Julian Morris, Antonia Borissova, Shahid Khan, Tariq Mahmud, Rado Penchev, Kevin J. Roberts). Near-infrared spectrometry using a LED diode-based light source thus proves to be particularly sensitive to temperature. Indeed, the emission spectrum of a LED diode varies significantly both in intensity and maximum peak wavelength shift, when the temperature only varies by a few degrees, as attested by the publication "Temperature Dependence Of LED and its Theoretical Effect on Pulse Oximetry", British Journal of Anaesthesia, 1991, Vol. 67, No 5 638-643 (K. J. Reynolds, B.A., M.SC., J. P. De Kock, B.A., L. Tarassenko, M.A., D. PHIL., C.EKG., M.I.E.E. and J. T. B. Moyle, M.B., B.S., I.ENG., M.rNST.M.c, M.I.E-LEC.I.E.).

However, a sensor associated with a heat engine, installed in particular on a vehicle, must be able to function within a very broad temperature range (depending on the application, present-day standards require a temperature range from −40° C. to +105° C., or even up to +150° C.). Furthermore, integrated sensors are supposed to ensure a long service life (depending on the application, present-day standards require a few thousand hours to several tens of thousands of hours). It is thus crucial to ensure the spectrometer functions correctly, to be able to manage in real time the influence of the temperature and of the aging of the light source to perform a qualitative determination of the product to be analyzed that is accurate and robust.

It is thus also desirable to produce a spectrometer having a stable spectral signal, and a signal/noise ratio as constant as possible, in a broad ambient temperature variation range and over a long length of operation.

Some embodiments relate to a method for controlling a spectrometer for analyzing a product, the spectrometer comprising a light source comprising several light-emitting diodes having respective emission spectra covering in combination an analysis wavelength band, the method comprising steps of: supplying at least one of the light-emitting diodes with a supply current to switch it on, and measuring a light intensity emitted by the light source by measuring a current at a terminal of at least another of the light-emitting diodes maintained off, determining, according to each light intensity measurement, a setpoint value of the supply current of each diode that is on, and regulating the supply current of each diode that is on so that it corresponds to the setpoint value.

According to one embodiment, the method comprises steps of successively switching on groups of at least one light-emitting diode, the diodes of a group having substantially identical emission spectra, while other light-emitting diodes are maintained off, of measuring a light intensity by each of the other light-emitting diodes maintained off, and of adjusting, according to each light intensity measurement obtained, the supply current setpoint value of the diode that is on.

According to one embodiment, the method comprises steps of: determining according to the light intensity measurements an integration time value of light-sensitive cells of a sensor of the spectrometer, disposed on a route of a light beam emitted by the light source and having interacted with a product to be analyzed, and if the integration time value and/or the supply current setpoint value of each diode that is on is between threshold values, supplying each diode that is on with a supply current regulated according to the value of the setpoint supply current, adjusting the integration time of each light-sensitive cell to the determined integration time value, and acquiring, by means of each cell of the sensor, light intensity measurements enabling a spectrum to be formed.

According to one embodiment, new setpoint values of supply current of each diode that is on and/or of integration time of each cell are determined and a supply current corresponding to the determined supply current setpoint value is supplied to each light-emitting diode that is on, as long as the determined integration time value is not between the threshold values.

According to one embodiment, the supply current setpoint of each light-emitting diode that is on is also adjusted according to a light intensity measurement supplied by a photodiode of the light source and/or to a measurement of the temperature of the light source, and/or a measurement of supply current intensity or voltage of each diode that is on.

According to one embodiment, the method comprises self-diagnosis test steps comprising at least one of the following comparisons: comparisons to determine whether the measurements of light intensity, and/or measurements of the supply current supplied to the diode that is on, and/or measurements of temperature of the light source are consistent with each other and with each supply current setpoint value of light-emitting diode that is on, comparisons of the setpoint value of the supply current supplied to each light-emitting diode that is on with minimum and maximum values, and if one of the comparisons reveals a defect, the spectrometer is switched to a degraded or default operating mode.

According to one embodiment, the method comprises a step of correcting the light intensity measurements taking account of a difference between the temperature of the product to be analyzed and/or the temperature of the sensor and a reference temperature, so as to obtain corrected light intensity measurements resulting from measurements taken at the reference temperature, the corrected measurements forming a corrected spectrum.

According to one embodiment, the method comprises steps of obtaining a corrected spectrum for each light-emitting diode, and of summing the corrected spectra obtained by applying weighting factors, to obtain a resulting spectrum, and possibly of calculating an average of several of the resulting spectra, the number of averaged spectra possibly depending on an operating mode, either normal or degraded, of the spectrometer.

According to one embodiment, the method comprises a calibration of the spectrometer, comprising: steps of determining minimum and maximum match values for matching light intensity measurements of a light flow produced by each light-emitting diode, with supply current setpoint values of each of the light-emitting diodes, and/or with temperature of the light source, and/or steps of determining minimum and maximum setpoint values of the supply current of the light source, and/or steps of determining minimum and maximum values of integration time of the light-sensitive cells of the sensor, and/or steps performed in the presence of one or more reference products, of determining a function supplying an optimal integration time of a light-sensitive cell of the sensor according to light intensity measurements of the light flow produced by each light-emitting diode, and/or steps performed in the presence of one or more reference products, during which the temperature of the light source and/or the temperature of the sensor and/or the temperature of the reference product is caused to vary independently, light intensity measurements supplied by the sensor, the setpoint values of the supply current of the diodes, and temperature measurements are collected, and a function supplying a corrected light intensity measurement corresponding to a reference temperature is determined, according to the measurements collected.

Some embodiments may also relate to a spectrometer comprising a light source emitting a light beam and comprising several light-emitting diodes having respective emission spectra covering in combination an analysis wavelength band, a sensor comprising light-sensitive cells disposed on a route of the light beam after it has interacted with a product to be analyzed, and a control device adjusting setpoint values of supply current of light-emitting diodes of the light source, and an integration time of the light-sensitive cells, the control device being configured to implement the method as previously defined.

According to one embodiment, the spectrometer is configured to switch on only one light-emitting diode of the light source at a time, and to collect a light intensity measurement by measuring a current at a terminal of each of the light-emitting diodes of the light source that are off.

According to one embodiment, the light source is configured to supply the control device with voltages and/or currents for supplying the light-emitting diodes.

According to one embodiment, the light-emitting diodes are integrated into a same electronic component, possibly with the photodiode and/or a temperature sensor.

According to one embodiment, the spectrometer comprises a temperature sensor supplying measurements of the temperature of the light source, and/or a temperature sensor supplying measurements of the temperature of the sensor, and/or a temperature sensor supplying measurements of the temperature of the product to be analyzed.

According to one embodiment, the spectrometer comprises a measurement cell wherein a product to be analyzed interacts with the light beam, an optical element to shape the beam at output of the light source and transmit it to the measurement cell, a wavelength filter configured to spatially spread the different wavelengths of the light beam at output of the measurement cell and transmit them to different light-sensitive cells of the sensor, the light source, the optical element, the measurement cell, the filter and the sensor being assembled so as not to form any air zone susceptible of being passed through by the light beam between the light source and the sensor.

Figure 2:
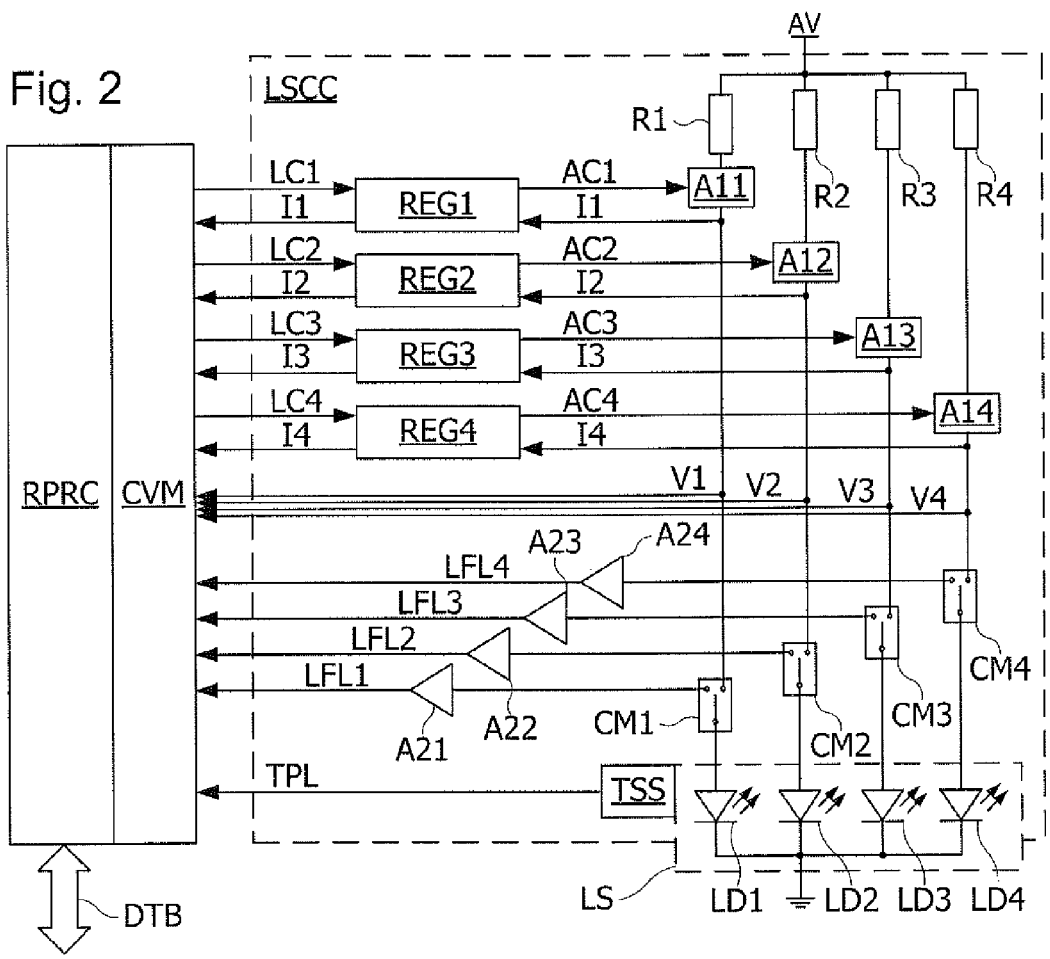
Figure 3A:
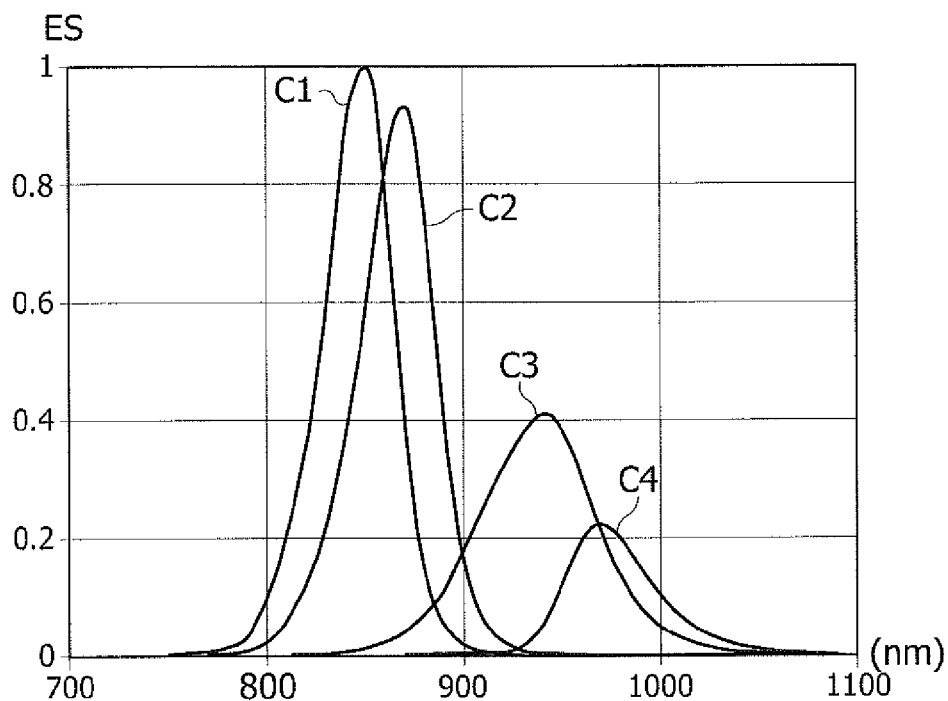
Figure 3B:
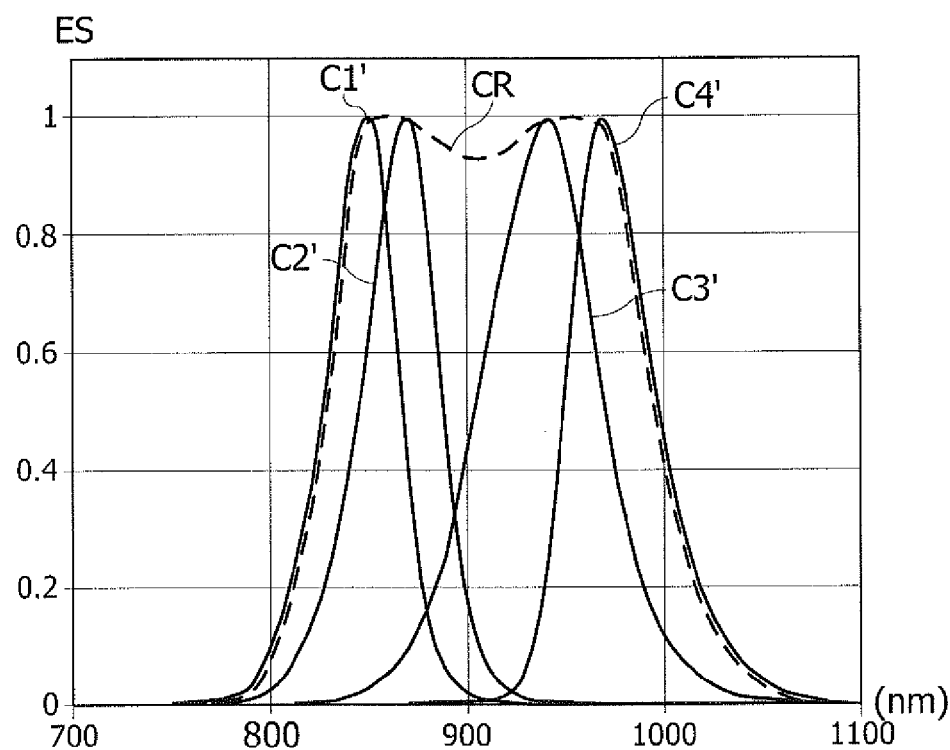
Figure 4:
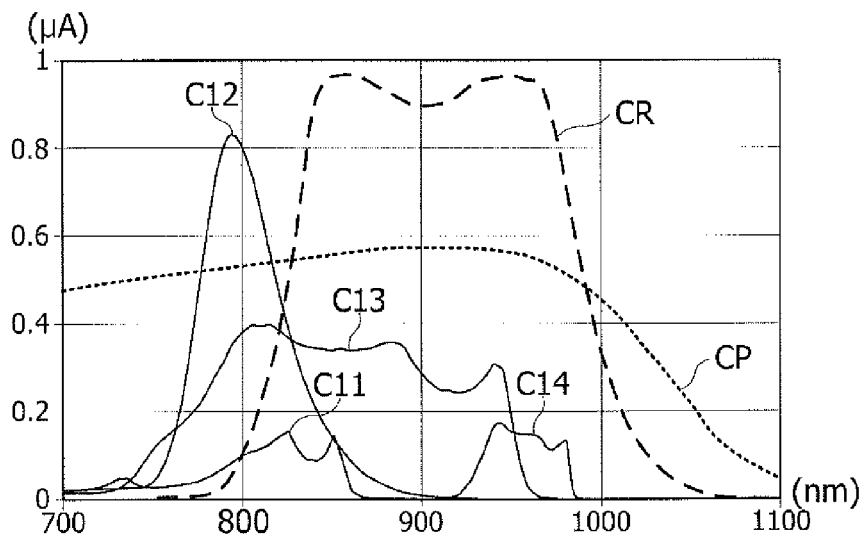
Figure 5:
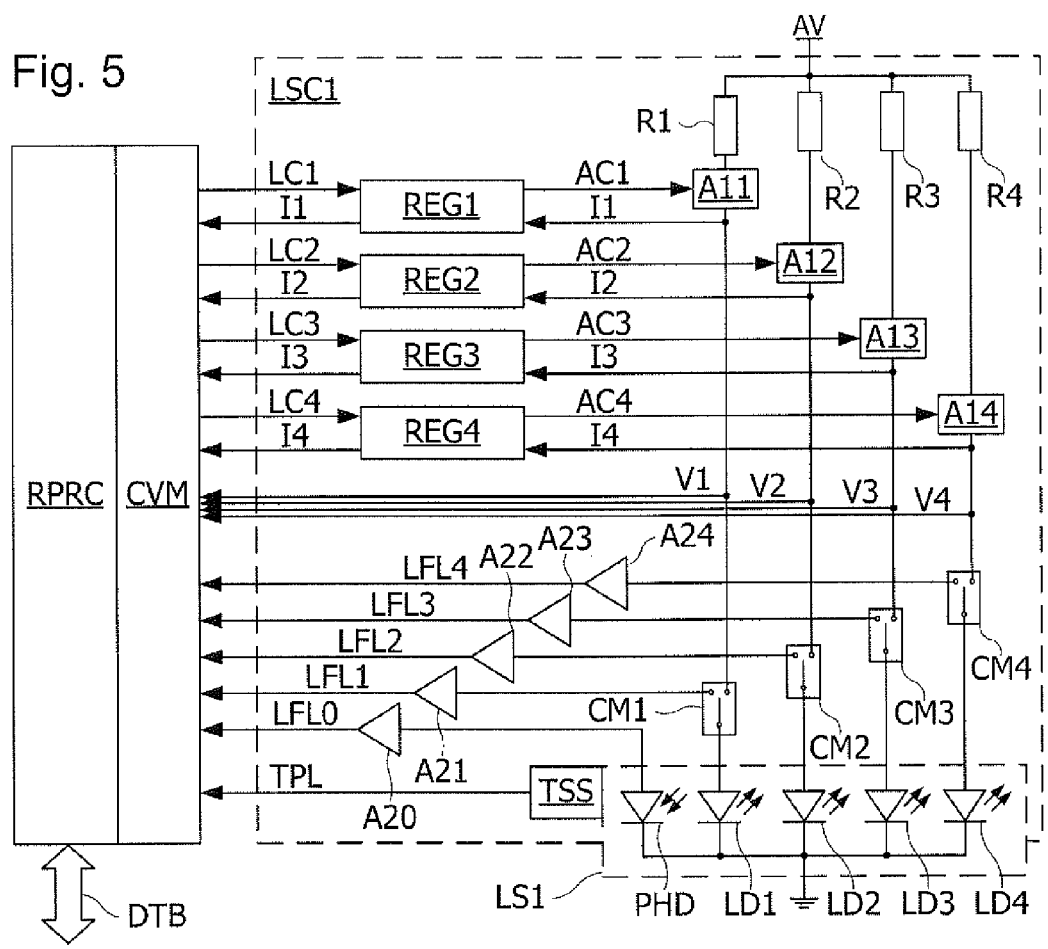
Figure 6:
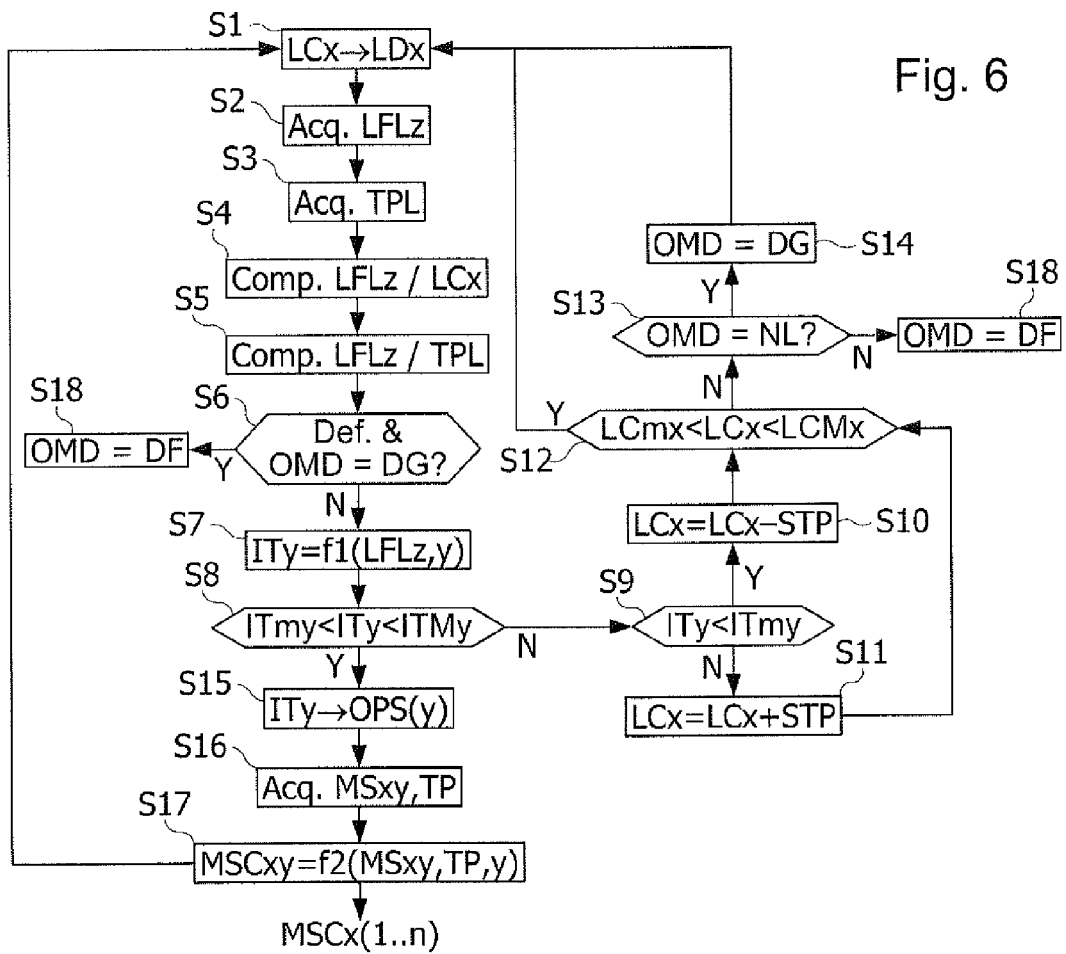
Figure 7:
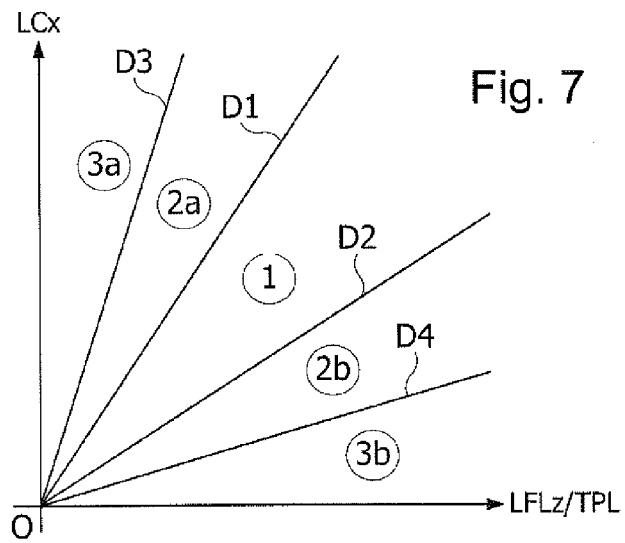

Some examples of embodiments of the present invention and of implementation of the method of the present invention will be described below, in relation with, but not limited to, the appended figures in which:

FIG. 1 schematically represents a spectrometer according to one embodiment,

FIG. 2 schematically represents an electronic control circuit for controlling a light source of the spectrometer, according to one embodiment, FIGS. 3A and 3B represent emission spectra of LED diodes, in the form of curves of the variation in light intensity emitted according to the wavelength, FIG. 4 represents sensitivity spectra of the LED diodes, in the form of curves of the variation in intensity of an electric current generated according to the wavelength, FIG. 5 schematically represents an electronic control circuit for controlling a light source of the spectrometer, according to another embodiment, FIG. 6 represents a sequence of steps executed by a regulating processor of the spectrometer, according to one embodiment, FIG. 7 represents a graph defining operating zones of the spectrometer.

FIG. 1 represents a spectrometer designed in particular to meet the specific requirements of a sensor installed on a vehicle or in a heat engine. The spectrometer comprises:
- a light source LS emitting a light beam LB,
- a lens-based optical element CLS to shape the beam LB produced by the source LS,
- a measurement cell FLC in which a product to be analyzed interacts with the beam LB,
- a wavelength filter WFL enabling the different wavelengths of the beam LB to be spatially spread at output of the cell FLC, and a sensor OPS that supplies measurements enabling a spectrum of the light at the output of the filter WFL to be constituted.

The light source LS covers at least one so-called "analysis" wavelength band in which the spectrum measurements must be taken. The optical element CLS transforms the geometry of the beam LB and introduces it into the measurement cell FLC. The optical element CLS may, for example, comprise a collimating lens which turns the beam LB into a beam with parallel rays. The cell FLC comprises an output window OPW sending the sensor OPS the light that has interacted with the product to be analyzed. The sensor OPS comprises several light-sensitive cells (n cells) and receives the light sent by the window OPW through the filter WFL. The filter WFL distributes the wavelengths making up the light sent by the measurement cell FLC over the light-sensitive cells of the sensor OPS, so that each cell of the sensor OPS receives only one small range of wavelengths belonging to the wavelength band corresponding to the spectrum to be generated. The filter WFL may, for example, be of Fabry-Perot type, or of variable linear type and generate a spatial spread of the wavelengths in the order of 20 to 50 nm/mm. The sensor OPS may be of CCD or CMOS type, and comprise an array of 20 to 200 light-sensitive cells.

The light source LS comprises one or more light-emitting diodes (p LED diodes), which may be integrated into a single electronic component associated with a single lens LLD focusing the light rays emitted by the diodes into a small solid-angle beam. The supply current, or the direct voltage of each of the LED diodes, can be electronically measured by conventional means well known to those skilled in the art. The light source LS can be fixed onto the optical element CLS through an optical block OB passed through by the light beam LB emitted by the source LS, so as not to trap air in the zone through which the beam passes. The optical block OB is transparent to the wavelengths to be analyzed and can be full or hollow and filled with an inert fluid. The lateral faces of the block OB, not passed through by the light beam coming from the source SL, may be covered with an opaque coating to prevent any light leakage via these faces.

The filter WFL is fixed onto the window OPW, so as not to trap air, directly or through an optical block having the same features as those of the optical block OB mentioned previously. Similarly, the filter WFL is fixed onto an input window of the sensor OPS so as not to trap air, directly or through an optical block which can have the same features as those of the optical block OB mentioned previously.

In this way, the spectrometer can be one-piece, which renders it easy to store and to industrially handle. The alignment of the different optical elements making up the spectrometer can thus be adjusted once and for all when manufacturing the spectrometer. The absence of air in the zone through which the light beam LB passes between the source LS and the sensor OPS also prevents any risk of water vapor condensation in this zone, as the presence of water droplets on the route of the beam LB can indeed disturb the analysis of the product in the measurement cell FLC.

The spectrometer is controlled by a control and regulation device RPRC which regulates the supply current LCx (x being a whole number ranging between 1 and p) of each LED diode of the light source LS, as well as an integration time ITy (y being a whole number ranging between 1 and n) of each light-sensitive cell y of the sensor OPS, depending on different parameters comprising at least one of the following parameters: intensities LFLx of light flow emitted by the LED diodes of the light source LS, the temperature TPL of the source LS, the temperature TPP of the product to be analyzed, and the temperature TPS of the sensor OPS. The integration time ITy of a light-sensitive cell corresponds to the time during which a potential well of the light-sensitive cell is left charging under the effect of a light flow.

According to one embodiment, the intensity LFLx of the light flow emitted by each LED diode of the source is measured by LED diodes of the source LS maintained off (receiving a zero supply current), only one or more of the LED diodes of the source LS being on at a given time. To generate a measurement spectrum, the LED diodes of the source are successively switched on by group of at least one LED diode, whereas each of at least one part of the LED diodes maintained off of the source LS is used as photodiode to measure the light intensity emitted by the source LS. As soon as a group of at least one LED diode is switched on, a spectrum is measured using the light-sensitive cells of the sensor OPS. When all the LED diodes have been switched on at least once, during a cycle of switching on the LED diodes, the spectra obtained are combined with each other to obtain the measurement spectrum sought.

According to one embodiment, the regulation device RPRC performs a regulation in looped mode, both of the supply current LCx of the LED diodes of the source LS, and of the integration time ITy of the light-sensitive cells of the sensor OPS. When the integration time ITy has reached a limit value, without obtaining any satisfactory signal (ranging between two limit values) at the output of the sensor OPS, the intensity or the voltage of the supply current LCx of the light source is adjusted. This regulation aims to stabilize the signal received by each of the light-sensitive cells of the sensor, and thus to minimize the impacts of factors external to the product to be analyzed itself, such as variations in the ambient temperature or the aging of the LED diodes of the source LS. This regulation aims to enable the spectrometer to function within a very broad temperature range, while keeping a signal/noise ratio relatively constant over time and homogeneous depending on the wavelength, and thus a substantially constant measurement sensitivity.

The integration time of the sensor OPS can be individually adjusted for each light-sensitive cell of the sensor OPS, or globally for all the light-sensitive cells, for example by choosing as global integration time, the minimum value of the integration times ITy determined for each of the cells y.

The regulation device RPRC receives a light intensity measurement MSy for each cell y of the sensor OPS, and can supply measurements MSCy corrected according to various parameters such as the temperature TPP of the product to be analyzed and/or the temperature TPS of the sensor OPS.

FIG. 2 represents an electronic control circuit LSCC of the light source LS, according to one embodiment. On FIG. 2, the circuit LSCC is connected to the source LS and is coupled to the regulation device RPRC through a conversion module CVM comprising several analog-digital converters and several digital-analog converters. The light source LS comprises several LED diodes LD1, LD2, LD3, LD4. The circuit LSCC comprises current regulation circuits REG1, REG2, REG3, REG4, adjustable gain amplifiers A11, A12, A13, A14, A21, A22, A23, A24, selector switches CM1, CM2, CM3, CM4 and resistors R1, R2, R3, R4. The cathode of each diode LD1 to LD4 is connected to the ground. The anode of each diode LD1 to LD4 is coupled through a respective selector switch CM1 to CM4, to the input of one of the amplifiers A21 to A24 and to the output of one of the amplifiers A11 to A14. The output of each of the amplifiers A21 to A24 is connected to the input of an analog-digital converter of the conversion module CVM, which sends the device RPRC digital values of light intensity measurements LFL1, LFL2, LFL3, LFL4 supplied by the diodes LD1 to LD4. Each amplifier A11 to A14 is coupled to a supply voltage source AV through one of the resistors R1 to R4. Each amplifier A11 to A14 receives at a gain control input a current control signal AC1 to AC4 emitted by one of the regulators REG1 to REG4. Each regulator REG1 to REG4 takes a measurement of the supply current I1 to I4 of the diode LD1 to LD4 to which it is connected. Each regulator REG1 to REG4 receives a setpoint current LC1 to LC4 value provided in digital form by the regulation device RPRC and converted by a digital-analog converter of the module CVM. Each regulator REG1 to REG4 regulates one of the current control signals AC1 to AC4 according to the value of the setpoint current LC1 to LC4 it receives and according to the intensity of the current I1 to I4 it measures at the output of the amplifier A1 to A4 the gain of which it controls, so that the current I1 to I4 measured corresponds to the value of the setpoint current LC1 to LC4.

The circuit LSCC or the light source LS may comprise a temperature sensor TSS to measure the temperature of the source LS. The temperature sensor TSS is then connected to an analog-digital converter of the module CVM, which supplies the device RPRC with digital values of temperature measurements TPL of the source LS.

Each regulator REG1 to REG4 may transmit the current intensity measurement I1 to I4 to an analog-digital converter of the module CVM, which in turn transmits a corresponding digital value to the device RPRC. Similarly, the anode of each diode LD1 to LD4 may also be connected to an analog-digital converter of the module CVM, which supplies the device RPRC with a digital value representative of the voltage V1 to V4 at the anode of the diode. Furthermore, the diodes LD1 to LD4 may be formed on a same semiconductor substrate integrated into a same component. The device RPRC may comprise a connector to connect, by means of a serial or parallel bus DTB, to a calculator and to transmit measurement spectra MR(1 . . . n) and an operating state OMD, and possibly other signals for example relating to the measurements taken on the spectrometer.

In the example in FIG. 2, the light source LS comprises four LED diodes. Each LED diode can send light having a spectrum having the shape of an unsymmetrical Gauss curve. Thus, FIG. 3A represents emission spectra of the diodes LD1 to LD4, in the form of curves C1 to C4 of variation of light intensity emitted according to the wavelength. The curves C1 to C4 in FIG. 3A have been obtained at constant and identical supply current for all the diodes LD1 to LD4. The light intensity values indicated on the Y-axis are standardized values. In the example in FIG. 3A, the curve C1 of the spectrum of the diode LD1 has a maximum intensity at 1 at a wavelength equal to approximately 850 nm. The curve C2 of the spectrum of the diode LD2 has a maximum intensity at approximately 0.92 at a wavelength equal to approximately 890 nm. The curve C3 of the spectrum of the diode LD3 has a maximum intensity at approximately 0.41 at a wavelength equal to approximately 940 nm. The curve C4 of the spectrum of the diode LD4 has a maximum intensity at approximately 0.22 at a wavelength equal to approximately 970 nm. It can be noted on FIG. 3A that the higher the wavelength of the maximum light intensity emitted by the diode LD1 to LD4, the lower this intensity is.

FIG. 3B represents in the form of curves C1' to C4' of variation of light intensity emitted according to the wavelength, the emission spectra of the diodes LD1 to LD4 after adjustment of the supply current LC1 to LC4 of each diode LD1 to LD4 by the regulation device RPRC. On FIG. 3B, all the curves C1' to C4' have a maximum standardized intensity value at 1. FIG. 3B also represents in the form of a curve CR, a combined emission spectrum emitted when the diodes LD1 to LD4 are switched on at the same time, with their supply current LC1 to LC4 adjusted. In the example in FIG. 3B, the combined emission spectrum of the light source ranges from approximately 840 to 980 nm. It shall be noted that the numeric values appearing in FIGS. 3A and 3B are given as an example and may vary particularly according to the manufacturing conditions of the diodes.

FIG. 4 represents sensitivity spectra of the diodes LD1 to LD4 in the form of curves C11 to C14 of variation in intensity of a current generated according to the wavelength. These spectra have been obtained by measuring the intensity of the current generated by each diode LD1 to LD4 when the photo-emitting surface of the latter is subjected to a light flow of 1 mW/cm$^2$ and in the absence of any supply current. According to FIG. 4, the current generated by the diodes LD1 to LD4 reaches a few tenths of μA when the diode is subjected to a light flow of 1 mW/cm$^2$.

According to one embodiment, the selector switches CM1 to CM4 are controlled so that only one of the diodes LD1 to LD4 is on at a time, the other diodes being off (not receiving any supply current) to function as photodiodes. Each of the diodes that are off supplies a measurement LFL1 to LFL4 (three measurements among four possible ones) of the light intensity generated by the diode that is on in their respective sensitivity spectrum. Once a measurement spectrum has been supplied by the sensor OPS with a diode on, the latter is switched off and another diode is switched on, and so on and so forth with the other diodes. The spectra obtained with each of the diodes on are then appropriately combined to obtain the resulting spectrum MR(1 . . . n).

It shall be noted that as only one diode LD1 to LD4 is on at a time, the circuit LSCC can be simplified by keeping only one of the regulators REG1 to REG4, and only one of the amplifiers A11 to A14. Each of the selector switches CM1 to CM4 then comprises a terminal connected to the output of the remaining amplifier A11 to A14, a terminal connected to the anode of a diode LD1 to LD4 and a terminal connected to the input of one of the amplifiers A21 to A24.

The selector switches CM1 to CM4 may be omitted if the regulators REG1-REG4 (or the remaining regulator) put their current input I1 to I4 to a floating potential and the amplifiers A11 to A13 (or the remaining amplifier) put their amplified current output to a floating potential.

Furthermore, the resulting emission spectrum (curve CR) may not be entirely covered by the combined sensitivity spectrum of the diodes LD1 to LD4. It can then be provided to use a photodiode measuring the light intensity directly emitted by each diode that is on. This photodiode may for example be integrated into the source LS.

Thus, FIG. 5 represents an electronic control circuit LSC1 for controlling a light source LS1, according to one embodiment. On FIG. 5, the light source LS1 differs from the light source LS in that it comprises a photodiode PHD. The circuit LSC1 differs from the circuit LSCC in that it comprises an additional amplifier A20 receiving the output signal from the photodiode PHD and supplying an analog-digital converter of the conversion module CVM with an electric signal of light intensity measurement LFL0. The digital value of the measurement LFL0 is used with the digital values of the measurements LFL1 to LFL4, by the regulation device RPRC to regulate the light intensity supplied by the source LS1. An example of photodiode sensitivity spectrum is represented in FIG. 4. Thus, FIG. 4 also has a curve CP of sensitivity of a photodiode that can be used in the circuit of FIG. 5. Indeed, the curve CP is substantially constant (varies between 0.5 and 0.6) in the analysis wavelength band, approximately between 840 and 980 nm.

FIG. 6 represents a sequence of steps which can be executed by the regulation device RPRC. On FIG. 6, the sequence of steps comprises steps S1 to S18. In step S1, the device RPRC adjusts to a setpoint value LCx the supply current (intensity or voltage) of a diode LDx of the light source LS (x being successively equal to 1, 2, 3 and 4 in the example in FIG. 2). The value LCx is that of a predefined initial value or a value previously applied to the diode LDx. In the next steps S2 and S3, the device RPRC receives light intensity measurements LFLz (z being different from x) coming from the diodes LD1-LD4 that are off, and possibly a light intensity measurement LFL0 coming from a photodiode and a temperature measurement TPL coming from the sensor TSS. In the next steps S4 and S5, the device RPRC determines by comparison whether the light intensity LFLz and temperature TPL measurements received are consistent with each other and with the current LCx supplied to the diode LDx. These steps can be performed from graphs of variation of the light intensity emitted by a diode LDx according to its supply current and its temperature. The comparisons performed in steps S4 and S5 enable a self-diagnosis of the spectrometer to be performed in step S6. Thus, if the comparisons performed in steps S4 and S5 reveal a malfunction and if the spectrometer is in a normal operating mode OMD, the spectrometer switches to a degraded DG operating mode OMD. If the comparisons performed in steps S4 and S5 reveal a malfunction and if the spectrometer is in a degraded DG operating state, the spectrometer goes to step S18 in a default mode DF in which it can no longer function. If the comparisons performed in steps S4 and S5 do not reveal any malfunction, the device RPRC executes the next steps S7 and S8. In step S7, the device RPRC determines an optimum integration time ITy of each light-sensitive cell y of the sensor OPS using a function f1 applied to the light intensities LFLz measured in step S2. The function f1 can be determined by graphs giving the optimum integration time of each cell y of the sensor OPS, according to intensity measurements of the emitted light LFLz supplied by each diode operating as photodiode. In step S8, the device RPRC compares for each cell y, the integration time ITy obtained at minimum ITmy and maximum ITMy values determined for the cell y. If the integration time ITy is between the minimum and maximum values ITmy, ITMy for each cell y, the device RPRC executes the steps S15 to S17 then returns to step S1 to execute a new regulation phase, otherwise it executes step S9.

In step S9, the device RPRC compares the optimum integration time ITy with the minimum integration time ITmy for each cell y for which the test in step S8 has not been checked. If the integration time ITy is lower than the integration time ITmy for all or part of the cells y of the sensor OPS, the module RPRC executes step S10, then step S12, otherwise (case where the integration time ITy is higher than the maximum integration time ITMy for all or part of the cells y) it executes steps S11 and S12. In step S10, the device RPRC decreases by one step STP the supply current LCx of the LED diode LDx. In step S11, the device RPRC increments the supply current LCx of the diode LDx by the step STP. In step S12, the device RPRC determines whether the new supply current LCx obtained in step S10 or S11 is between minimum LCmx and maximum LCMx values determined for the diode LDx. If this is the case, the device RPRC returns to step S1 to execute a new regulation phase. In the opposite case, the device RPRC executes step S13 where it tests the operating mode OMD of the spectrometer. If the mode OMD is normal NL, the device RPRC executes step S14 wherein the operating mode OMD switches to degraded mode DG. If in step S13, the mode OMD is degraded DG, the device RPRC executes step S18, wherein the mode OMD switches to default DF.

Thus, in steps S10 and S11, if the optimal integration time STy determined for at least one light-sensitive cell y is outside the minimum and maximum thresholds ITmy and ITMy, a step STP of a given amplitude, either positive or negative (positive if the optimal integration time ITy is higher than the maximum threshold ITMy, and negative if this integration time is lower than the minimum threshold ITmy) is added to the supply current LCx of the LED diode LDx. A new optimal integration time ITy is then again determined in steps S1 to S7 according to the new current LCx. The execution of steps S1 to S12 is repeated until the optimal integration time ITy is no longer outside thresholds ITmy and ITMy and until the current LCx is no longer between the thresholds LCmx and LCMx.

In step S15, the device RPRC sets the integration time of each cell y of the sensor OPS to its optimum integration time ITy determined in step S7. In step S16, the device RPRC proceeds with the acquisition of a measurement MSxy supplied by each cell y with the diode LDx on, as well as possibly, of a measurement of the temperature TP of the product to be analyzed in the measurement cell FLC (TPP) and/or of a temperature measurement of the sensor OPS (TPS) and/or a temperature measurement of the source LS (TPL). In step S17, the device RPRC applies a correction to each measurement MSxy using a function f2 and provides a corrected measurement MSCxy for each cell y. The function f2 is applied to the temperature TP measured (or to the temperatures measured) in step S16.

The sequence of steps S1 to S18 thus enables a corrected spectrum MSCx(1 . . . n) to be obtained for each diode LDx. The sequence of steps S1 to S15 is thus executed for each diode LDx of the source LS so as to obtain at least one spectrum MSCx(1 ... n) for each diode LDx. After a standardization of the spectra obtained for each diode, a resulting spectrum MR(1 ... n) is calculated by adding up the spectra obtained with each diode LDx on, with a weighting factor Pxy specified for each diode LDx and each cell y of the sensor OPS:

$$MRy = \sum_x Pxy \cdot MSCxy \quad (1)$$

The weighting factors Pxy can be adjusted so as to give more importance to the useful signal in the resulting spectrum. In other words, the signals of the cells y measuring the highest raw signals, and thus supplying the most reliable information (high signal to noise ratio), are associated with a higher weighting factor Pxy. The weighting coefficients Pxy are determined during the calibration phase and depend on the temperature TPL of the source LS.

An average calculation can further be performed on the resulting spectrum MR(1 ... n) obtained with several other successive spectra obtained, so as to obtain a spectrum that is usable by a device for regulating the operating parameters of a heat engine. The number of spectra MR(1 ... n) used for this average calculation may be increased when switching from the normal NL operating mode OMD to the degraded mode DG. The number of spectra obtained to be averaged in normal mode can be in the order of 5 to 20, and in degraded mode, in the order of 100.

It shall be noted that the integration time ITy of all the light-sensitive cells y of the sensor OPS can, in step S15, be globally set to the lowest integration time determined in step S7 for each cell y.

In steps S4, S5, S6, S12, S13, S14 and S18, the device RPRC performs a self-diagnosis of the spectrometer by distinguishing three operating modes OMD of the spectrometer: the normal operating mode NL in which the spectrometer produces usable measurements, the degraded operating mode DG in which the spectrometer still produces usable measurements, but in abnormal conditions, and a default mode DF in which the spectrometer is considered defective and can no longer supply any usable measurement. In the degraded mode DG, the time for supplying a measurement is clearly increased or the level of trust in the measurements supplied decreases (may be chosen by the user). The spectrometer is considered in default (mode OMD=DF) for example when the light intensity measurements LFLz supplied by the diodes LD1-LD4 that are off do not correspond to the current LCx supplied to the diode that is on, or to the temperature TPS of the source LS. The device RPRC can send a self-diagnosis signal indicating the operating mode OMD of the spectrometer. This signal can be transmitted for example to a computer in the vehicle in which the spectrometer is installed.

FIG. 7 represents a graph of the setpoint current LCx supplied to a LED diode LDx of the source LS (Y-axis) according to measurements of light intensity LFLz or of temperature TPL of the source LS (X-axis). This graph has four straight lines D1, D2, D3, D4 passing through the origin O of the graph. The straight lines D1 and D2 delimit between them a zone 1 of operation corresponding to the normal operating mode NL in which the current LCx supplied to a LED diode LDx of the source LS, the temperature TPL of the source and/or the light intensities LFLz measured have normal values (neither too low nor too high). The Y-axis and the straight line D3 delimit a zone 3a between them. The X-axis and the straight line D2 D3 delimit a zone 3b between them. The zones 3a and 3b correspond to the default mode DF in which the current LCx supplied to a diode LDx of the light source is high and the light intensity supplied by the source is abnormally low, or in which the current supplied to the diode LDx is low and the temperature of the source TPL is abnormally high. Between the zone 1 and the zones 3a and 3b there are zones 2a and 2b corresponding to the degraded operating mode DG.

The minimum LCmx and maximum LCMx values of the supply current of each diode LDx, result from tests performed during a calibration phase to determine the ideal operating range of each of the light-emitting diodes of the source LS. The maximum value LCMx is determined so as not to speed up the aging of the diode. The minimum value LCmx can be chosen so as to ensure repeatability and stability of the light flow emitted by the diode.

The minimum ITmy and maximum ITMy values of each cell y of the sensor OPS are also determined during the calibration phase by tests enabling an ideal operating range of the light-sensitive cells y of the sensor OPS, considered independently or as a whole, to be determined. The maximum value ITMy is determined so as to avoid a saturation of the light-sensitive cell y. The minimum value ITmy is determined so as to obtain a stable and repeatable signal, while respecting a minimum target signal/noise ratio value as previously defined.

Similarly, the functions f1 and f2 used in steps S7 and S17 can be determined during the calibration phase. Thus, the function f1 giving the optimal integration time ITy of each cell y of the sensor OPS according to the light intensities LFLz measured by the diodes LD1-LD4 that are off, can be determined using one or more fluid or solid reference products with which a series of tests is performed. For each of the reference products and each LED diode LDx, the supply current setpoint value LCx of the diode LDx is caused to vary, and the light intensities LFLz measured by the off diodes LD1-LD4 and the possible photodiode PHD are stored. For each light intensity measurement LFLz value and each cell y, an optimal integration time ITy is sought enabling a stable and constant light flow measured by the cell y to be obtained, i.e. substantially independent of the intensity of the light flow emitted by the source LS. Groups of measurements (light intensities LFLz-optimal integration time ITy) are thus obtained. With each group of measurements, the temperature of the source TPL, if available, is also collected, as well as the temperature of the product TPP and the setpoint of the corresponding current LCx. The variations in the light intensities LFLz measured by each diode LD1-LD4 that is off and/or by the possible photodiode PHD are such that for a portion of the measurements taken, the optimal integration time ITy is outside the predefined threshold values ITmy, ITMy. From the groups of measurements, either look-up tables, or graphs, or prediction models are established, enabling the optimal integration time ITy of each cell y to be determined according to the light intensities LFLz measured. From the data thus collected, minimum and maximum match values are determined between the light intensity measurements LFLz, and the temperature TPL of the source LS (if the latter is available), and between the light intensity measurements LFLz and the value of the supply current LCx of the LED diode LDx on. These minimum and maximum match values are used in steps S4 and S5 to perform a self-diagnosis of the spectrometer.

The function f2 enabling the measurement of the light intensity MSxy supplied by each cell y according to the temperature TP to be corrected can be determined by a series of tests during which the temperature TPL of the source LS, the temperature TPS of the sensor OPS and the temperature TPP of the product to be analyzed is caused to vary in an independent manner. These temperatures extend from −40 to +105° C., or ideally from −50 to +150° C. with at least one fluid or solid reference product. For each of the tests, the measurement values of intensity MSxy, of setpoint current LCx and of temperature are collected. From these measurements, either look-up tables, or graphs, or prediction models are established, enabling, for each light-sensitive cell y of the sensor OPS, the light intensity that this cell would have measured at a given fixed reference temperature (for example 20° C.) to be determined, so as to obtain a corrected spectrum independent of the ambient temperature conditions and of the temperature conditions of the components of the spectrometer. The graphs obtained enable a corrected light intensity measurement MSCxy to be determined at the reference temperature according to the light intensity measurement MSxy taken at the ambient temperature by each light-sensitive cell y, according to the temperatures TPL, TPP, TPS of the source LS, of the product in the measurement cell FLC and of the sensor OPS, and according to the integration time ITy and to the supply current LCx of the LED diode LDx. Some of the parameters previously listed may not be taken into account, and in particular the temperature TPS of the sensor OPS, particularly if the latter is equipped with an efficient temperature compensation.

Thanks to the spectrum transposition performed to reduce the measured spectrum MSx(1 . . . n) to a spectrum MSCx(1 . . . n) that would have been obtained at a reference temperature, the spectrometer that has just been described can thus function within a very broad temperature range, including with very significant temperature differences between the product to be analyzed and the light source LS. It shall be noted that this arrangement is obtained without using any complex reference channel requiring a second sensor which directly receives the light emitted by the source, as proposed in the FR patent application 2 940 447, but only with measurements of light intensity LFL0-LFL4 directly performed on the light flow emitted by the diodes LD1-LD4, thus at lower cost and without increasing the size of the spectrometer.

Instead of being based on the light intensities LFL0-LFL4 measured by the diodes LD1-LD4 that are off and/or the photodiode PHD, the regulation performed by the sequence of steps S1 to S18 can be carried out based on the temperature of the source TPL and/or of the product to be analyzed TPP, or even based on the voltages Vx or currents Ix (x ranging between 1 and 4 in the example of FIG. 2) measured in the circuit of FIG. 2. In addition, the light intensity measurements LFL1-LFL4 supplied by the diodes that are off, the temperature TPL and/or the voltages Vx and/or the currents Ix can be used to check the proper operation of the photodiode PHD and of the temperature sensor TSS.

It will be understood by those skilled in the art that the present invention is susceptible of various alternative embodiments and various applications. In particular, the control method is not limited to using light-emitting diodes as light source. Indeed, the regulation method described above can apply to any light source of which the emitted light intensity can be adjusted by the supply current of the light source.

Furthermore, the control method may apply to other spectrometers than the one described with reference to FIG. 1. It is merely important that the integration time of the sensor of the spectrometer can be adjusted, and that the spectrometer can supply measurements representative of the operation of the light source.

The step of correcting the spectrum measurements obtained to take account of the temperature of the various components of the spectrometer is not necessary either. It is indeed possible to consider placing the spectrometer in an enclosure the temperature of which is kept constant, or only taking a spectrum measurement when the temperature of the spectrometer has reached a setpoint temperature.

The light source may comprise several groups of several light-emitting diodes having identical or substantially identical emission spectra, i.e. subject to differences due to manufacturing. The result is that several diodes, i.e. all the diodes of each group, can be switched on at the same time.

The invention claimed is:

1. A method for controlling a spectrometer for analyzing a product, the spectrometer comprising a light source comprising several light-emitting diodes having respective emission spectra covering in combination an analysis wavelength band, the method comprising:
supplying a first light-emitting diode of the light-emitting diodes with a supply current to switch the first light-emitting diode on;
measuring a current at a terminal of a second light-emitting diode of the light-emitting diodes that is maintained off, whereas the second light-emitting diode receives light from the first light-emitting diode that is on;
determining, from the current measured at the terminal, a light intensity emitted by the first light-emitting diode;
determining, according to the determined light intensity, a supply current setpoint value of the supply current supplied to the first light-emitting diode that is on, such that the light intensity of the light emitted by the light source corresponds to a light intensity setpoint value;
regulating the supply current of the first light-emitting diode that is on so that it corresponds to the current setpoint value; and
acquiring, by means of light-sensitive cells of a sensor of the spectrometer, disposed on a route of a light beam emitted by the light source and having interacted with a product to be analyzed, light intensity measurements enabling a spectrum to be formed.

2. The method of claim 1, wherein the light-emitting diodes of the spectrometer comprise several groups of light-emitting diodes, the light-emitting diodes of each of the groups having substantially identical emission spectra, the first light-emitting diode belonging to a first one of the groups and the second light-emitting diode belonging to a second one of the groups, the method further comprising:
successively supplying each of the groups with the supply current to switch on the light-emitting diodes of the group, whereas the other light-emitting diodes are maintained off.

3. The method of claim 1, further comprising:
determining according to the determined light intensity, an integration time value of the light-sensitive cells of the sensor; and
in the event that the integration time value is between threshold values, supplying each light-emitting diode that is on with a supply current regulated according to the current setpoint value; and
adjusting the integration time of each light-sensitive cell to the determined integration time value.

4. The method of claim 3, wherein a new current setpoint value is determined for each light-emitting diode that is on, and a supply current corresponding to the determined current setpoint value is supplied to each light-emitting diode that is on, as long as the determined integration time value is not between the threshold values.

5. The method of claim 1, wherein the current setpoint value of each light-emitting diode that is on is adjusted according to the determined light intensity.

6. The method of claim 1, comprising further comprising:
performing a self-diagnosis test,
wherein performing the self-diagnosis test comprises at least one of the following comparisons:
(i) comparisons to determine whether the measurements of light intensity are consistent with each other and with each supply current setpoint value of light-emitting diode that is on,
(ii) comparisons to determine whether measurements of the supply current supplied to the diode that is on, are consistent with each other and with each supply current setpoint value of light-emitting diode that is on,
(iii) comparisons to determine Whether measurements of temperature of the light source are consistent with each other, and
(iv) comparisons of the current setpoint value of the supply current supplied to each light-emitting diode that is on with minimum and maximum values,
wherein if one of the comparisons (i), (ii), (iii) or (iv) reveals a defect, the spectrometer is switched to a degraded or default operating mode.

7. The method of claim 1, further comprising:
correcting the light intensity measurements taking account of a difference between a temperature within the spectrometer and a reference temperature, so as to obtain corrected light intensity measurements resulting from measurements taken at the reference temperature, the corrected measurements forming a corrected spectrum.

8. The method of claim 7, further comprising:
obtaining a corrected spectrum for each light-emitting diode, and of summing the corrected spectra obtained by applying weighting factors, to obtain a resulting spectrum.

9. The method of claim 8, further comprising:
calculating an average of several of the resulting spectra, the number of averaged spectra depending on an operating mode, either normal or degraded, of the spectrometer.

10. The method of claim 1, further comprising:
performing a calibration of the spectrometer,
wherein performing the calibration of the spectrometer comprises at least one of the following calibration operations;
determining minimum and maximum match values for matching light intensity measurements of a light flow produced by each light-emitting diode, with setpoint values of the supply current of each of the light-emitting diodes;
determining minimum and maximum match values for matching light intensity measurements of a light flow produced by each light-emitting diode with the temperature of the light source;
determining minimum and maximum setpoint values of the supply current of the light source;
determining minimum and maximum values of integration time of the light-sensitive cells of the sensor;
determining, in the presence of one or more reference products, a function supplying an optimal integration time of a light-sensitive cell of the sensor according to light intensity measurements of the light flow produced by each light-emitting diode; and
performing a calibration operation, performed in the presence of one or more reference products, the calibration operation comprising: (i) varying a temperature within the spectrometer, (ii) collecting light intensity measurements supplied by the sensor, the setpoint values of the supply current of the diodes, and temperature measurements, and (iii) determining a function supplying a corrected light intensity measurement corresponding to a reference temperature, according to the measurements collected.

11. The method of claim 1, further comprising:
determining according to the determined light intensity an integration time value of the light-sensitive cells of the sensor; and
in the event that the supply current setpoint value of each light-emitting diode that is on is between threshold values, supplying each light-emitting diode that is on with a supply current regulated according to the current setpoint value, and adjusting the integration time of each light-sensitive cell to the determined integration time value.

12. The method of claim 11, wherein a new integration time value for each cell is determined and a supply current corresponding to the determined current setpoint value is supplied to each light-emitting diode that is on, as long as the determined integration time value is not between the threshold values.

13. The method of claim 1, wherein the supply current setpoint of each light-emitting diode that is on is adjusted according to a measurement of the temperature of the light source.

14. The method of claim 1, wherein the current setpoint value of each light-emitting diode that is on is adjusted according to a measurement of supply current intensity or supply current voltage of each diode that is on.

15. A spectrometer comprising:
a light source emitting a light beam and comprising several light-emitting diodes having respective emission spectra covering in combination an analysis wavelength band;
a sensor comprising light-sensitive cells disposed on a route of the light beam after it has interacted with a product to be analyzed; and
a control device controlling the light-emitting diodes of the light source, and the light-sensitive cells,
wherein the control device is configured to:
supply a first light-emitting diode of the light-emitting diodes with a supply current to switch the first light-emitting diode on;
measure a current at a terminal of a second light-emitting diode of the light-emitting diodes that is maintained off, whereas the second light-emitting diode receives light from the first light-emitting diode that is on;
determine, from the current measured at the terminal, a light intensity emitted by the first light-emitting diode;
determine, according to the determined light intensity, a supply current setpoint value of the supply current supplied to the first light-emitting diode that is on, such that the light intensity of the light emitted by the light source corresponds to a light intensity setpoint value;

regulate the supply current of the first light-emitting diode that is on so that it corresponds to the current setpoint value; and acquire, by means of light-sensitive cells of a sensor of the spectrometer, disposed on a route of a light beam emitted by the light source and having interacted with a product to be analyzed, light intensity measurements enabling a spectrum to be formed.

16. The spectrometer of claim 15, configured to switch on only one light-emitting diode of the light source at a time, and to collect a light intensity measurement by measuring a current at a terminal of each of the light-emitting diodes of the light source that are off.

17. The spectrometer of claim 15, wherein the light source is configured to supply the control device with voltages and/or currents for supplying the light-emitting diodes.

18. The spectrometer of claim 17, wherein the light-emitting diodes are integrated into a same electronic component.

19. The spectrometer of claim 17, wherein the light-emitting diodes are integrated into a same electronic component, with the photodiode and a temperature sensor.

20. The spectrometer of claim 15, further comprising:
a temperature sensor supplying measurements of the temperature of at least one of the light source and the sensor.

21. The spectrometer of claim 15, further comprising:
a measurement cell,
wherein a product to be analyzed interacts with the light beam, an optical element to shape the beam at output of the light source and transmit it to the measurement cell, a wavelength filter configured to spatially spread the different wavelengths of the light beam at output of the measurement cell and transmit them to different light-sensitive cells of the sensor the light source, the optical element, the measurement cell, the filter and the sensor being assembled so as not to form any air zone susceptible of being passed through by the light beam between the light source and the sensor.

22. The spectrometer of claim 15, further comprising:
a temperature sensor supplying measurements of the temperature of the product to be analyzed.

23. The spectrometer of claim 15, wherein
the light-emitting diodes of the light source comprise several groups of light-emitting diodes, the light-emitting diodes of each of the groups having substantially identical emission spectra,
the first light-emitting diode belongs to a first one of the groups and the second light-emitting diode belonging to a second one of the groups,
the control device is configured to successively supply each of the groups with the supply current to switch on the light-emitting diodes of the group, whereas the other light-emitting diodes are maintained off.

24. The spectrometer of claim 15, wherein the control device is further configured to:
determine, according to the determined light intensity, an integration time value of the light-sensitive cells of the sensor; and
in the event that the integration time value is between threshold values, supply each light-emitting diode that is on with a supply current regulated according to the current setpoint value; and adjust the integration time of each light-sensitive cell to the determined integration time value.

25. The spectrometer of claim 24, wherein the control device is further configured to:
determine a new integration time value for each cell and supply a supply current corresponding to the determined current setpoint value to each light-emitting diode that is on, as long as the determined integration time value is not between the threshold values.

26. The spectrometer of claim 15, wherein the control device is further configured to:
determine a new current setpoint value for each light-emitting diode that is on; and
supply a supply current corresponding to the determined supply current setpoint value to each light-emitting diode that is on, as long as the determined integration time value is not between the threshold values.

27. The spectrometer of claim 26, wherein the control device is further configured to:
adjust the current setpoint value of each light-emitting diode that is on, according to the determined light intensity.

28. The spectrometer of claim 15, wherein the control device is further configured to:
adjust the current setpoint value of each light-emitting diode that is on according to a measurement of the temperature of the light source.

29. The spectrometer of claim 15, wherein the control device is further configured to:
adjust the current setpoint value of each light-emitting diode that is on according to a measurement of supply current intensity or supply current voltage of each diode that is on.

30. The spectrometer of claim 15, wherein the control device is further configured to:
perform a self-diagnosis test comprising at least one of the following comparisons:
(i) comparisons to determine whether the measurements of light intensity, are consistent with each other and with each supply current setpoint value of light-emitting diode that is on,
(ii) comparisons to determine whether measurements of the supply current supplied to the diode that is on, are consistent with each other and with each supply current setpoint value of light-emitting diode that is on,
(iii) comparisons to determine whether measurements of temperature of the light source are consistent with each other, and
(iv) comparisons of the setpoint value of the supply current supplied to each light-emitting diode that is on with minimum and maximum values,
wherein if one of the comparisons (i), (ii), (iii) or (iv) reveals a defect, the spectrometer is switched to a degraded or default operating mode.

31. The spectrometer of claim 15, wherein the control device is further configured to:
correct the light intensity measurements taking account of a difference between a temperature within the spectrometer and a reference temperature, so as to obtain corrected light intensity measurements resulting from measurements taken at the reference temperature, the corrected measurements forming a corrected spectrum.

32. The spectrometer of claim 31, wherein the control device is further configured to:
calculate an average of several of the resulting spectra, the number of averaged spectra depending on an operating mode, either normal or degraded, of the spectrometer.

33. The spectrometer of claim 15, wherein the control device is further configured to:
  obtain a corrected spectrum for each light-emitting diode, and sum the corrected spectra obtained by applying weighting factors, to obtain a resulting spectrum.

34. The spectrometer of claim 15, wherein the control device is further configured to:
  perform a calibration of the spectrometer,
  wherein performing the calibration operation comprises at least one of the following calibration operations:
    determining minimum and maximum match values for matching light intensity measurements of a light flow produced by each light-emitting diode, with setpoint values of the supply current of each of the light-emitting diodes;
    determining minimum and maximum match values for matching light intensity measurements of a light flow produced by each light-emitting diode with the temperature of the light source;
    determining minimum and maximum setpoint values of the supply current of the light source;
    determining minimum and maximum values of integration time of the light-sensitive cells of the sensor;
    determining, in the presence of one or more reference products, a function supplying an optimal integration time of a light-sensitive cell of the sensor according to light intensity measurements of the light flow produced by each light-emitting diode, and
  performing a calibration operation, performed in the presence of one or more reference products, the calibration operation comprising: (i) varying a temperature within the spectrometer, (ii) collecting light intensity measurements supplied by the sensor, the setpoint values of the supply current of the diodes, and temperature measurements, and (iii) determining a function supplying a corrected light intensity measurement corresponding to a reference temperature, according to the measurements collected.

* * * * *